United States Patent [19]

White

[11] Patent Number: 4,642,399
[45] Date of Patent: Feb. 10, 1987

[54] METHOD FOR PRODUCING FLUORONITROBENZENE COMPOUNDS

[75] Inventor: Carl R. White, St. Louis, Mo.

[73] Assignee: Mallinckrodt, Inc., St. Louis, Mo.

[21] Appl. No.: 676,117

[22] Filed: Nov. 29, 1984

[51] Int. Cl.[4] ............................................. C07C 79/12
[52] U.S. Cl. ...................................... 568/938; 568/937
[58] Field of Search ................ 568/937, 938; 260/694; 564/417

[56] References Cited

U.S. PATENT DOCUMENTS

| | | | |
|---|---|---|---|
| 3,064,058 | 11/1962 | Duesel et al. | 568/937 |
| 3,240,824 | 3/1966 | Boudakian et al. | 568/937 |
| 3,992,432 | 11/1976 | Napier et al. | 260/465.1 |
| 4,069,262 | 1/1978 | Kunz | 568/937 |
| 4,140,719 | 2/1979 | Tull et al. | 564/417 |
| 4,164,517 | 8/1979 | Fuller | 568/938 |
| 4,226,811 | 10/1980 | Oeser et al. | 568/937 |
| 4,229,365 | 10/1980 | Oeser et al. | 568/937 |
| 4,252,739 | 2/1981 | Fayter, Jr. et al. | 568/939 |
| 4,287,374 | 9/1981 | North | 568/937 |
| 4,418,229 | 11/1983 | White | 568/938 |

FOREIGN PATENT DOCUMENTS

| | | | |
|---|---|---|---|
| 38726 | 3/1982 | Japan | 568/938 |
| 1469700 | 4/1975 | United Kingdom. | |
| 2042507 | 9/1980 | United Kingdom | 568/937 |
| 2058067 | 4/1981 | United Kingdom | 568/937 |

OTHER PUBLICATIONS

Starks, "Selecting a Phase Transfer Catalyst"–Chemtech, Feb. 1980, pp. 110–117.

G. C. Finger et al., J. Am. Chem. Soc. 78, 6034–6037 (1956).

Primary Examiner—Stephen J. Lechert, Jr.
Assistant Examiner—Anne Brookes
Attorney, Agent, or Firm—R. G. Jackson; L. N. Goodwin; R. J. Klostermann

[57] ABSTRACT

A method is disclosed for producing fluoronitrobenzene compounds by reacting chloronitrobenzene compounds with a fluoride salt in the presence of a tetramethylammonium salt phase-transfer catalyst. This catalyst allows the use of elevated reaction temperatures with substantial freedom from catalyst inactivation, resulting in yields and reaction rates which are improved over those of previously known methods using higher molecular weight quaternary ammonium salt phase transfer catalysts having more total carbon atoms in their ammonium cations.

16 Claims, No Drawings

METHOD FOR PRODUCING FLUORONITROBENZENE COMPOUNDS

BACKGROUND OF THE INVENTION

The present invention relates to a method for producing fluoronitrobenzene compounds.

Fluoronitrobenzene compounds such as 2-fluoronitrobenzene, 4-fluoronitrobenzene, and 2,4-difluoronitrobenzene, are useful as intermediates for the synthesis of various herbicidal compounds, dyes, and the like. Such compounds have been prepared from corresponding chloronitrobenzene compounds by so-called halogen exchange reactions, illustrated as follows:

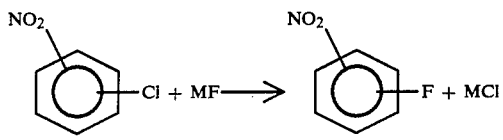

wherein MF represents an alkali metal fluoride salt. The reaction is generally conducted in an aprotic, polar, organic solvent, such as dimethylsulfoxide, dimethylformamide, tetramethylenesulfone (sulfolane), and the like.

Alkali metal fluoride salts are not soluble in such solvents. Therefore, the reaction mixtures usually contain two phases, i.e., solid and liquid phases or two immiscible liquid phases. Finger, et al., *J. Am. Chem Soc.*, 78, 6034 (1956) and Duesel, et al., U.S. Pat. No. 3,064,058 (1962), describe the reaction of chloronitrobenzene compounds with finely-divided, solid potassium fluoride in aprotic polar solvents to produce corresponding fluoronitrobenzene compounds. Boudakian, et al., U.S. Pat. No. 3,240,824 (1966), describe the reaction of o-chloronitrobenzene with solid potassium fluoride at elevated temperatures, without any solvent or diluents, to produce o-fluoronitrobenzene. Napier and Starks, U.S. Pat. No. 3,992,432 (1976), describe a reaction involving two liquid phases. In the Napier and Starks reaction, the inorganic fluoride salt is dissolved in an aqueous phase, and the chloronitrobenzene compound is dissolved in a water-immiscible, organic phase. The reaction is catalyzed by a quaternary salt, which reportedly transfers ions across the phase interface.

Use of quaternary salt phase-transfer catalysts in solid-liquid, two phase reactions also has been known. For instance, Kunz, U.S. Pat. No. 4,069,262 (1978), describes the production of 2-fluoronitrobenzene by reacting 2-chloronitrobenzene with ultrafine particulate potassium fluoride in tetramethylenesulfone solvent using a macrocyclic ether (crown ether) or a quaternary ammonium halide (such as tetrabutylammonium chloride, benzyltrimethylammonium chloride, benzyltrimethylammonium fluoride or benzyltriethylammonium chloride) as the catalyst.

Tull, et al., U.S. Pat. No. 4,140,719 (1979), describes the production of 2,4-difluoro-5-chloronitrobenzene by reacting 2,4,5-trichloronitrobenzene with a solid fluorinating agent selected from NaF, KF, CsF, and $C_{1-4}$ alkyl quaternary ammonium fluoride, and mixtures thereof under substantially anhydrous conditions in the presence of a quaternary compound solid-liquid phase transfer catalyst. The liquid phase comprises an organic solvent in which the trichloro compound is soluble and the fluorinating agent is essentially insoluble. It is disclosed that, for example, the quaternary catalyst compound must be soluble in toluene and accordingly the four radicals in the catalyst compound must be selected so that the total number of carbon atoms is at least 18. In a list of quaternary compounds which may be employed as transfer catalysts, the total number of carbon atoms ranges from 26 (for trioctylethylammonium bromide) to 38 (for dioctadecyldimethylammonium chloride).

Starks, "Selecting a Phase Transfer Catalyst," *Chemtech* (Feb. 1980), pages 110–117, describes patterns that purportedly enable prediction of catalysts for anion transfer from aqueous or solid inorganic phases to organic phases. Starks mentions "the normally used 14–30 carbon" catalyst cations (p. 114) and refers to the cations $(C_8H_{17})_3NCH_3{}^+$, $(C_4H_9)_4N^+$, $C_{16}H_{33}P(C_4H_9)_3{}^+$, $(C_6H_5CH_2N(C_2H_5)_3{}^+$ and $(C_{16}H_{33})N(CH_3)_3{}^+$ as those most frequently used in quaternary salt catalysis (p. 110). According to Starks, "In order to have anion transfer, the phase transfer cation plus the desired anion must be substantially partitioned into the organic phase" (p. 113) and a quaternary cation having few carbon atoms "usually will not be sufficiently lipophilic to effect transfer, unless the organic phase is highly polar and the anion to be transferred has a substantial organic structure" (p. 114).

North, U.S. Pat. No. 4,287,374 (1981) discloses a process for the production of a monofluoronitrobenzene in which a monochloronitrobenzene is heated with an alkali metal fluoride and a phase transfer catalyst at a temperature of no more than 200° C., preferably 125°–170° C., especially 140°–150° C. North discloses, as examples of such catalysts which may be used, long chain alkylammonium halides, e.g., tetradecyltrimethylammonium bromide (which has 17 carbon atoms), aralkylammonium compounds, e.g., benzyltriethylammonium chloride or hydroxide (which have 13 carbon atoms) and alkylphosphonium halides, e.g., hexadecyltributylphosphonium bromide (which has 28 carbon atoms). Organic polar aprotic solvents, e.g., dimethylsulfoxide, dimethylformamide or sulpholane, reportedly can be used.

In general, halide-exchange reactions for preparing fluoronitrobenzene compounds by reacting chloronitrobenzene compounds with fluoride salts in aprotic, polar organic solvents in the presence of quaternary ammonium salt phase-transfer catalysts proceed at faster rates when conducted at elevated temperature relative to rates obtainable at lower temperature. However, quaternary ammonium phase-transfer catalysts employed in heretofore known methods are less stable at higher temperature and have been found to decompose or lose their catalytic activity at elevated reaction temperatures. Moreover, U.S. Pat. No. 4,418,229 (to White), incorporated herein by reference, discloses that lower molecular weight catalysts, i.e., those having a total number of carbon atoms less than about 16, are less stable under the conditions (including elevated temperature) of the method of the invention disclosed therein than the therein preferred catalysts of higher molecular weight having about 16 or more carbon atoms. Quaternary ammonium salt phase transfer catalysts such as tetrabutylammonium halides, e.g., $(C_4H_9)_4NBr$ and $(C_4H_9)_4NCl$, cetyltrimethylammonium halides, e.g., $C_{16}H_{33}(CH_3)_3NBr$ and $C_{16}H_{33}(CH_3)_3NCl$, and Aliquat ® 336 (available from McKerson Corp., Minneapolis, Minn. and designated chemically as tricaprylmethylammonium chloride) have been found to decompose rapidly at elevated temperature (e.g., 170°–175°

C.) with concomitant rapid substantial depletion of catalytic activity (e.g., in less than one half hour).

The above cited White patent discloses the finding that in the conversion of chloronitrobenzene compounds to corresponding fluoronitrobenzene compounds using a quaternary ammonium salt phase-transfer catalyst at elevated temperatures, a high level of catalytic activity can be maintained by adding the catalyst to the reaction mixture incrementally during the course of the reaction.

DESCRIPTION OF THE INVENTION

It has now been unexpectedly and surprisingly found that in the conversion of chloronitrobenzene compounds to corresponding fluoronitrobenzene compounds using a quaternary ammonium salt phase-transfer catalyst at elevated temperatures, a high level of catalytic activity can be maintained by using a tetramethylammonium salt as the catalyst without need for incremental addition thereof to the reaction mixture. It has also been unexpectedly found that tetramethylammonium salts do not decompose appreciably at elevated temperature in the reaction mixture described hereinbelow and result in substantially increased reaction rate relative to reaction rates obtainable with quaternary ammonium salts containing more carbon atoms, such as tetrabutylammonium bromide, cetyltrimethylammonium bromide and Aliquat® 336. Accordingly, elevated reaction temperatures, which result in substantial deactivation of high-carbon quaternary ammonium salt phase-transfer catalysts employed in heretofore known methods for effecting such conversion may be employed for good reaction rates and yields. The effective life of a given amount of this catalyst is substantially extended, and yet the reaction rate is not significantly reduced at high temperatures.

Generally stated, the present invention provides an improved method for producing fluoronitrobenzene compounds which includes reacting a chloronitrobenzene compound with a fluoride salt in a substantially anhydrous, aprotic, polar organic solvent under halide-exchange conditions in the presence of a catalyzing amount of a quaternary ammonium salt phase-transfer catalyst, wherein the improvement comprises using a tetramethylammonium salt (hereinafter sometimes referred to as TMA salt) as the phase-transfer catalyst.

The use of TMA salt, e.g., $(CH_3)_4NCl$ (hereinafter sometimes referred to as TMAC), as the catalyst allows use of an elevated reaction temperature with substantial freedom from inactivation of the catalyst, resulting in good reaction rates and yields. The improved method is also effective for the conservation of catalyst at such elevated temperatures.

DETAILED DESCRIPTON OF THE INVENTION AND OF THE MANNER AND PROCESS OF USING IT

The halide-exchange conditions generally include elevated reaction temperatures, which are high enough to provide sufficient energy of activation for the reaction. Although such reaction temperatures might cause some catalyst inactivation, the temperature is preferably not so high as to cause rapid decay of catalytic activity or substantial decompostion of the reactants, the products, or the solvent. Although the reaction temperature may vary, depending upon the particular catalyst, solvent, and reactants used, generally it may be, for example, from about 120° C. to about 220° C., preferably from about 150° C. to about 180° C., and more preferably from about 170° C. to about 175° C.

Those skilled in the art will appreciate that a variety of equipment and techniques may be utilized in the method of the present invention, and the invention is not limited to any particular equipment or technique. The method is generally conducted by charging the reactants, solvent and TMA salt catalyst into a reaction vessel which is equipped with agitating and heating means. Advantageously, the entire amount of the reactants, solvent and TMA salt catalyst to be employed can be added initially. The reaction vessel may also advantageously include a reflux condenser or other means of recovering solvent vapors and means for blanketing the reaction mixture with a dry inert gas, e.g., nitrogen. The reaction mixture is heated to the desired reaction temperature and agitated.

The halide-exchange reaction conditions employed in the present invention advantageously include substantially anhydrous reaction conditions. The presence of water in the reaction can diminish yields and result in undesirable by-products. Various techniques may be used for dehydrating the reactants and solvent, such as vacuum drying, azeotropic distillation, chemical drying and the like. Azeotropic distillation, for example with benzene, has been used for drying all of the reactants and solvents; however, any convenient and operable technique may be employed. Due to the deleterious effect of water, the reaction mixture is preferably substantially devoid of water. Small amounts of water may be tolerated; however, a corresponding reduction in yield is generally experienced. Advantageously, the concentration of water in the reaction mixture is below about 5 wt. % and is preferably below about 1 wt. %, based on the weight of the reaction mixture.

The solvent for the catalyst, chloronitrobenzene compound, and fluoronitrobenzene compound is an aprotic, polar, organic solvent, which preferably has a relatively high boiling point, e.g., a boiling point above about 190° C. Lower boiling solvents may be used; however, pressure reactors may be required for their containment. Solvents having boiling points below a desired reaction temperature may be employed by conducting the reaction under superatmospheric pressure in such reactors. Examples of reaction solvents include dimethylsulfoxide, sulfolane, bis(2-methoxyethyl)ether, bis 2-(2-methoxyethoxy) ethyl ether, hexamethylphosphoramide, N-methylpyrolidinone, and dimethylformamide. Dimethylsulfoxide and sulfolane are preferred solvents. Sulfolane is most preferred from the standpoint of commercial attractiveness.

The phase-transfer catalyst employed in the present method is a tetramethylammonium salt which is soluble in the reaction solvent in an amount sufficient to catalyze the reaction. Such salt may be represented by the formula:

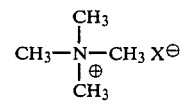

wherein $X^-$ may be an anion which dissociates from the ammonium ion in the reaction solvent, e.g., chloride, fluoride, bromide, iodide, nitrate, bisulfate, and the like. $X^-$ is preferably a halide, especially chloride or fluoride. The TMA salt is most preferably tetramethyl ammonium chloride. The TMA salt may be employed in any catalyzing amount, i.e., in any amount effective for catalyzing the conversion of the chloronitrobenzene compound to the corresponding fluoronitrobenzene compound. In general, the amount may correspond, for example, to a molar ratio of TMA salt to chloronitrobenzene compound of from about 0.005:1 to about 0.5:1, preferably from about 0.04:1 to about 0.15:1, most preferably about 0.08:1. In general, amounts of TMA salt corresponding to molar ratios of less than about 0.005:1 may not provide sufficient catalytic activity, while amounts corresponding to molar ratios of more than 0.5:1 may result in insufficient additional benefit to justify the additional cost. As indicated above, the entire amount of TMA salt to be employed may be added initially. However, if desired, a portion may be added initially with incremental addition of the remainder during the course of the reaction. Incremental addition may be, for example, substantially in accordance with the invention disclosed in the above-cited White patent.

The fluoride ion is provided by an alkali metal fluoride salt which is generally present in an amount at least substantially stoichiometric to the chloronitrobenzene reactant. Preferred fluoride salts are potassium fluoride, rubidium fluoride, and cesium fluoride, and potassium fluoride is particularly preferred. The fluoride salt is advantageously finely-divided, to provide a greater superficial surface area which is accessible to the catalyst and the chloronitrobenzene compound. Preferred concentrations of the fluoride salt range from about 1 to about 2 times the stoichiometric amount, most preferably from about 1.2 to about 1.6 times such amount. For example, in a method for producing a monofluoronitrobenzene compound, a preferred molar ratio of fluoride salt to chloronitrobenzene compound is about 1.5:1. Lower concentrations of fluoride salts can result in diminished reaction rates, and, although higher concentrations can be used, no appreciable benefit is generally realized therefrom.

In the chloronitrobenzene compound used as a starting material in the present invention, the relative positions of the nitro and chloro substituents, and the presence of other substituents on the ring can affect the reactivity of the starting compound. Generally, halogen exchange reactions involve compounds in which the chloride is in the ortho or para position with respect to the nitro group, and reactivity may increase when other electron-withdrawing groups are present on the ring. Compounds having chloro substituents in the meta as well as ortho and/or para positions may be used as starting materials, but usually only the chloro groups in the ortho and para positions will undergo halogen exchange. Accordingly, the method of this invention may be used for example for the synthesis of compounds such as 2-fluoronitrobenzene, 2-fluoro-3-chloronitrobenzene, 4-fluoronitrobenzene, 2,4-difluoronitrobenzene, 5-chloro-2,4-difluoronitrobenzene, and the like, from corresponding chloronitrobenzene compounds. The present method is particularly useful for the preparation of 4-fluoronitrobenzene from 4-chloronitrobenzene and 2-fluoronitrobenzene from 2-chloronitrobenzene.

The reaction is generally allowed to proceed until substantially all the chloronitrobenzene compound has been converted to the corresponding fluoronitrobenzene compound. A reaction time of from about 10 minutes to about 20 hours may typically be used, and the reaction will often be substantially complete after about 1 to about 6 hours. After the reaction is completed, the product can be recovered by any suitable procedure, such as extraction, distillation, steam distillation and the like. For some purposes, the purity of the crude reaction product, recovered as an organic phase after addition of water to the reaction mixture, will be satisfactory.

The method of this invention has been found to produce fluoronitrobenzene compounds in good yields with little formation of by-products. The invention is further illustrated by the following examples, which are not intended to be limiting.

EXAMPLE I

A three-necked, round bottom flask which was equipped with an overhead drive stirrer, thermometer and reflux condenser was thoroughly purged with nitrogen. While maintaining the nitrogen blanket, 4-chloronitrobenzene (200 g., 1.27 moles), and dimethylsulfoxide (297 g, 3.81 mol) were charged to the reaction flask. Anhydrous potassium fluoride (110 g, 1.90 mol) and tetramethylammonium chloride (12.0 g, 0.11 mol), both of which had been dried for one hour at 100° C. and 25" Hg, were then added. The reaction mixture was heated to 170°–175° C. and maintained in that range for three hours with stirring. The reaction liquor was cooled to about 90° C. and deionized water (200 ml) was added. The reaction flask was equipped with distillation equipment and the contents heated to boiling. The distillate, thus obtained, consisted of water and 4-fluoronitrobenzene. Deionized water was added to the reaction flask during the distillation in order to maintain a pot temperature of 115°–116° C. The distillation was continued until a single phase distillate was obtained. A total of about 1200 ml of distillate was collected. The distillate was transferred to a separatory funnel and the organic layer was separated. The aqueous layer was extracted 1×100 and 1×50 ml of dichloromethane. The combined extracts were stripped of dichloromethane on a rotovap. The yield of technical grade 4-fluoronitrobenzene thus obtained was 163 g. A gas chromatography assay indicated the product was 98% pure which represents a 90% yield.

EXAMPLE II 4-chloronitrobenzene (200 g, 1.27 mol), dimethylsulfoxide (297 g, 3.81 mol), vacuum dried potassium fluoride (110 g, 1.90 mol) and vacuum dried tetramethylammonium chloride (3.0 g, 0.03 mol) were charged to a reaction flask and heated to 170°–175° C. While maintaining the reaction mixture at such temperature and with stirring, the progress of the reaction was followed by sampling the liquor every 30 minutes and analyzing each sample by gas chromatography using the following conditions: column packing—10% Bentone 34 on 80–100 mesh Gas Chroma A; Column Temperature—180° C.; Injection volume—2 microliters; Detector—flame ionization. For, each sample, the PA-FNB (the peak area of the fluoronitrobenzene product) and the PA-CNB (the peak area of the residual chloronitrobenzene reactant) where measured. The area percent of the fluoronitrobenzene was calculated from the following equation: Area Percent=(PA−FNB) 100% / (PA−FNB+PA−CNB). The results are presented below:

| TIME, HOUR | AREA PERCENT OF 4-FLUORONITROBENZENE |
|---|---|
| 0.5 | 53.9 |
| 1.0 | 65.9 |
| 1.5 | 73.2 |
| 2.0 | 77.7 |
| 2.5 | 79.3 |
| 3.0 | 83.5 |

EXAMPLE III

The procedure for Example II was repeated except that 9.0 g (0.08 mol) of tetramethylammonium chloride was used. The gas chromatography results are presented below:

| TIME, HOURS | AREA PERCENT OF 4-FLUORONITROBENZENE |
|---|---|
| 0.5 | 80.7 |
| 1.0 | 88.5 |
| 1.5 | 91.3 |
| 2.0 | 95.8 |
| 2.5 | 96.3 |
| 3.0 | 97.5 |

EXAMPLE IV

The procedure of Example I was repeated except that 2-chloronitrobenzene was reacted to produce 2-fluoronitrobenzene. The progress of the reaction as determined by the gas chromatography procedure of Example II is presented below:

| TIME, HOURS | AREA PERCENT OF 2-FLUORONITROBENZENE |
|---|---|
| 0.5 | 64.0 |
| 1.0 | 79.3 |
| 1.5 | 85.7 |
| 2.0 | 90.7 |
| 2.5 | 93.8 |
| 3.0 | 96.3 |
| 3.5 | 97.7 |
| 4.0 | 98.7 |

The yield of technical grade 2-fluoronitrobenzene was 161 g, (90%).

EXAMPLE V

2-Chloronitrobenzene (78.8 g, 0.50 mol), vacuum dried potassium fluoride (43.5 g, 0.75 mol), sulfolane (180.0 g, 1.50 mol) and vacuum dried tetramethylammonium chloride (4.4 g, 0.04 mol) were heated to 170°–175° C. and maintained at that temperature for six hours with stirring. The reaction liquor was cooled to less than 50° C. and filtered to remove the potassium salts. The filter cake was washed several times with dichloromethane (150 ml). The dichloromethane was distilled at atmospheric pressure and then the product was collected by fractional distillation at 83°–90° C. at 7.5 mm pressure using a fractionating column of ten theoretical plates. The yield of 2-fluoronitrobenzene was 49.0 g (70%).

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. In a method for producing a fluoronitrobenzene compound by reacting a corresponding chloronitrobenzene compound with a fluoride salt in a reaction mixture comprising an aprotic, polar, organic solvent under halogen-exchange conditions in the presence of a catalyzing amount of a quaternary ammonium salt phase-transfer catalyst, the improvement comprising, in combination, (a) said fluoride salt consists essentially of an alkali metal fluoride salt and (b) said phase-transfer catalyst consists essentially of a teramethylammonium salt in an amount effective for catalyzing the reaction of said chloronitrobenzene compound with said alkali metal fluoride salt to produce said fluoronitrobenzene compound.

2. The method of claim 1, wherein said tetramethylammonium salt is added to the reaction mixture in a molar ratio of said tetramethylammonium salt to said chloronitrobenzene compound from about 0.005:1 to about 0.5:1.

3. The method of claim 2, wherein said ratio is from about 0.04:1 to about 0.15:1.

4. The method of claim 1, wherein the fluoronitrobenzene compound is selected from the group consisting of 2-fluoronitrobenzene, 2-fluoro-3-chloronitrobenzene, 4-fluoronitrobenzene, 2,4-difluoronitrobenzene, and 2,4-difluoro-5-chloro-nitrobenzene.

5. The method of claim 1, wherein the fluoronitrobenzene compound is 2-fluoronitrobenzene.

6. The method of claim 1, wherein the fluoronitrobenzene compound is 4-fluoronitrobenzene.

7. The method of claim 5 or 6, wherein the halogen-exchange conditions include an elevated reaction temperature of from about 150° C. to about 180° C.; the reaction mixture contains less than about 5% water; the polar organic solvent is dimethylsulfoxide or sulfolane; the fluoride salt is finely divided potassium fluoride; and the reaction is conducted for from about 1 to about 6 hours.

8. The method of claim 1, wherein the halogen-exchange conditions include an elevated reaction temperature of from about 120° C. to about 220° C.; the reaction mixture contains less than about 5% water; the polar organic solvent is selected from the group consisting of dimethylsulfoxide, sulfolane, bis(2-methoxyethyl)ether, bis (2-methoxyethoxy)ethyl ether, hexamethylphosphoramide, N-methyl-pyrolidinone and dimethylforamide; and the alkali metal fluoride salt is selected from the group consisting of potassium fluoride, rubidium fluoride and cesium fluoride.

9. The method of claim 1, wherein the halogen exchange conditions include an elevated reaction temperature of from about 150° C. to about 180° C.; the reaction mixture contains less than about 5 wt. % water; the polar, organic solvent is dimethylsulfoxide or sulfolane; and the fluoride salt is finely divided potassium fluoride.

10. The method of claim 1, wherein the polar organic solvent is dimethylsulfoxide.

11. The method of claim 1, wherein the polar organic solvent is sulfolane.

12. The method of claim 10 or 11, wherein the reaction temperature is from about 170° C. to about 175° C.

13. The method of claim 1, wherein all the tetramethylammonium salt is added initially.

14. The method of claim 1, wherein the anion of said tetramethylammonium salt is selected from the group consisting of chloride, fluoride, bromide, iodide, nitrate, and bisulfate.

15. The method of claim 14, wherein the anion of said tetramethylammonium salt is selected from the group consisting of chloride, bromide, iodide, nitrate, and bisulfate.

16. The method of claim 15, wherein said tetramethylammonium salt is tetramethyl ammonium chloride.

* * * * *